US012649039B2

(12) United States Patent
Chien et al.

(10) Patent No.: US 12,649,039 B2
(45) Date of Patent: Jun. 9, 2026

(54) PATIENT INTERFACE

(71) Applicant: Wellell Inc., New Taipei City (TW)

(72) Inventors: Chih-Tsan Chien, New Taipei City
(TW); Shu-Chi Lin, New Taipei City
(TW); Yi-Ting Tseng, New Taipei City
(TW)

(73) Assignee: WELLELL INC., New Taipei City
(TW)

( * ) Notice: Subject to any disclaimer, the term of this
patent is extended or adjusted under 35
U.S.C. 154(b) by 942 days.

(21) Appl. No.: 17/886,853

(22) Filed: Aug. 12, 2022

(65) Prior Publication Data

US 2023/0057539 A1    Feb. 23, 2023

Related U.S. Application Data

(60) Provisional application No. 63/233,777, filed on Aug.
17, 2021.

(51) Int. Cl.
A61M 16/06 (2006.01)
A61M 16/08 (2006.01)

(52) U.S. Cl.
CPC .... A61M 16/0683 (2013.01); A61M 16/0622
(2014.02); A61M 16/0816 (2013.01)

(58) Field of Classification Search
CPC .......... A61M 16/0683; A61M 16/0622; A61M
16/0816; A61M 16/0666
See application file for complete search history.

(56) References Cited

U.S. PATENT DOCUMENTS

2013/0037030 A1*    2/2013   Matula, Jr. ........ A61M 16/0666
128/205.25

FOREIGN PATENT DOCUMENTS

CA           3084203 A1 *   6/2011   ........ A61M 16/0057
WO    WO-2006072128 A1 *   7/2006   ........ A61M 16/0683

* cited by examiner

*Primary Examiner* — Elliot S Ruddie
(74) *Attorney, Agent, or Firm* — WPAT, PC

(57) ABSTRACT

A patient interface including a headgear and a frame assembly is provided. The headgear is for maintaining the patient interface on a head of a patient. The frame assembly is for connecting to the headgear, and includes a main frame, and two side extension arms respectively extending from two sides of the main frame. When no force is applied to the side extension arm, an upper edge of a cheek contact section of the extension arm is closer to a mask central axis of the patient interface than a lower edge, so that the upper edge of the cheek contact section is away from an apex of a cheekbone of the patient when the patient interface is worn. The patient interface of the present invention better complies to a face by using the two side extension arms that conform to a profile of positions of upper halves of cheekbones of the face, and provides effects of good support and stability as well as dispersed weight and pressure.

17 Claims, 15 Drawing Sheets

(a)

(b)

(c)

(d)

(e)

PATIENT INTERFACE

CROSS REFERENCE TO RELATED APPLICATION

The present application claims priority to U.S. Provisional Patent Application No. 63/233,777 filed on Aug. 17, 2021, the entire content of which is incorporated by reference to this application.

BACKGROUND OF THE INVENTION

Field of the Invention

The present invention relates to a patient interface, and more particularly, to a patient interface used for a continuous positive airway pressure (CPAP) respirator.

Description of the Prior Art

A continuous positive airway pressure (CPAP) respirator is equipment used for treating obstructive sleep apnea (OSA). By sealing a nose of a patient or sealing both a mount and a nose of a patient using a patient interface, air or other breathable gas is continuously supplied to the patient, and a continuous positive pressure is maintained to open up congested airways of the patent and keep the airways unobstructed, further achieving an object treating OSA.

When in use, the patient interface is maintained on the of a patient by the headgear. The patient interface generally includes a frame and a cushion. The softer cushion forms an air chamber having a positive pressure around the nose and/or the mouth, such that airtightness is formed on the cheeks or around the nostrils by contacting and coupling of the cushion. In general, a patient feels less sensation of a foreign object as a contact area between the patient interface and the face of the patient gets smaller, and hence a high level of comfort. However, as the contact area reduces, the stability of the patient interface may also reduce to even affect treatment effects. Thus, a more rigid frame is needed to provide support. Taking a nasal pillow patient interface for example, in order to enable the patient interface to be stably worn at the head of a patient, the frame forms an intense binding force of the headgear by pulling the headgear or using a highly stretchable headgear so as to press the cushion around the nostrils of the patient, and a portion of the frame or the headgear is abutted against the cheeks and extends to above the ears along the cheekbones. However, when worn for an extended period of time, the intensive binding force of the headgear causes overly large compression around the nostrils and the cheeks of the patient, leading to wearing discomfort. Moreover, due to the weight of the patient interface or the overall configuration of airflow pipelines, the center of gravity of the patient interface is biased toward to the front of the wearer. If a portion of the frame or the headgear extends only along below the cheekbones and only is abutted against only the cheeks of the patient, the patient interface cannot be easily supported by this portion of the frame or the headgear. Moreover, the cushion of which the center of gravity is also closer to the front of the wearer may be easily shifted downward to produce an inappropriate pressurizing force on the philtrum and upper lip of the wearer, further contributing to one main reason causing severe discomfort. In addition, when a patient sleeps sideways, the frame and the headgear can be easily pressed and thus become deformed or shifted, such that the cushion departs the position around the nostrils and no longer provides airtightness. All of the reasons above may reduce the compliance of a patient using the patient interface for the treatment of OSA, resulting in treatment effects that are not as good as anticipated. Therefore, there is a need to provide a stable patient interface capable of appropriately dispersing a pressure on a face.

SUMMARY OF THE INVENTION

It is an object of the present invention to provide a patient interface having an enhanced wearing stability and capable of appropriately dispersing a pressure on a face of a patient.

To achieve the above and other objects, the present invention discloses a patient interface for delivering air to airways of a patient. The patient interface may include a headgear and a frame assembly. The headgear is adapted to maintain the patient interface on a head of the patient. The frame assembly is adapted to connect to the headgear, and includes a main frame, and two side extension arms respectively extending from two sides of the main frame. When no force is applied to the side extension arm, an upper edge of a cheek contact section of the extension arm is closer to a mask central axis of the patient interface than a lower edge, so that the upper edge of the cheek contact section is away from an apex of a cheekbone of the patient when the patient interface is worn.

In one embodiment of the present invention, when the patient interface is worn, the upper edge of the cheek contact section is closer to an eye socket (aka, orbit) of the patient than the lower edge.

In one embodiment of the present invention, when the patient interface is worn, the upper edge of the cheek contact section is closer to a median sagittal plane of the patient than the lower edge.

In one embodiment of the present invention, the patient interface may further include a cushion assembly, an elbow assembly and an adaptor member. The cushion assembly is configured to form an air chamber having a positive environment near an entrance of the airway of the patient. The elbow assembly is adapted to deliver air generated by a fluid generator to the air chamber of the cushion assembly. The adaptor member is adapted to connect the frame assembly, the cushion assembly and the cushion assembly. A center of an air inlet of the elbow assembly and a center of an installation hole of the adaptor member form the mask central axis.

In one embodiment of the present invention, when the patient interface is worn, the cheek contact section may abut against an upper position of the cheekbone of the cheek of the patient and is away from a lower position of the cheekbone of the cheek of the patient.

In one embodiment of the present invention, each side extension arm may have a first end close to a main frame and a second end away from the main frame, and a shortest distance between an upper edge and a lower edge of the first end is smaller than a shortest distance between an upper edge and a lower edge of the second end.

In one embodiment of the present invention, each side extension arm may further include a frame connecting section and a turning portion. The frame connecting section is adapted to connect at the main frame, and the turning portion is located between the frame connecting section and the cheek contact section, such that the cheek contact section gets away from the central axis of the mask of the patient interface along a lengthwise extension direction.

In one embodiment of the present invention, each side extension arm may be rotatably connected on the main frame.

In one embodiment of the present invention, each side extension arm may further include a headgear connecting section for connecting the headgear.

In one embodiment of the present invention, the headgear may include two side straps, a top strap and a back strap. The top strap is connected between the two side straps, and each side strap is for detachably attaching to the headgear connecting sections of the two side extension arms. During wearing, the top strap can cross over the top of the head of the patient, and the back strap can be located on the position of an occipital bone of the patient.

In one embodiment of the present invention, in the headgear, the back strap may have an elastic section, and an elongation rate of the elastic section can be greater than that of other parts of the back strap.

In one embodiment of the present invention, in the headgear, the width of the back strap is wider in the middle and narrower on two sides.

In one embodiment of the present invention, in the headgear, the width of the top strap is wider in the middle and narrower on two sides.

To achieve the above and other objects, the present invention discloses a patient interface including a cushion assembly and a pair of side extension arms. The cushion assembly is configured to form an air chamber having a positive environment near an entrance of an airway of a patient. The pair of side extension arms are neighboring to two sides of the cushion assembly, and each of the side extension arm may have a cheek contact section. During wearing, the cheek contact sections are between apexes of cheekbones and eye sockets of the patient, and fit to upper edges of upper halves of the left and right cheekbones of the patient, so as to avoid the apexes of the cheekbones and lower halves of the cheekbones of the patient.

In one embodiment of the present invention, the upper edge of the cheek contact section is closer to a median sagittal plane of the patient than the lower edge.

In one embodiment of the present invention, each side extension arm may be made of a flexible material.

In one embodiment of the present invention, each side extension arm may have a turning portion between the nose and the cheekbone of the patient. The turning portion has a change in curvature greater than a change in curvature of other parts of the side extension arm, and is adapted to support near a nose wing of the patient.

In one embodiment of the present invention, the width of the turning portion may be greater than the widths of other parts of the side extension arm.

In one embodiment of the present invention, a connecting line between top and bottom apexes of the turning portion may be non-perpendicular to a tangent of an upper edge of the side extension arm, and non-perpendicular to a tangent of a lower edge of the side extension arm.

In one embodiment of the present invention, the cushion assembly may be inserted into nostrils, sealed in the nostrils or sealed near the nostrils of the patient.

Accordingly, the patient interface of the embodiments of the present invention has two downwardly and outwardly everted side extension arms so as to be closely attached to the upper halves of the cheekbones on the face, hence providing the patient interface with better support to prevent the mask from sliding down or drooping. Thus, the headgear is kept with an appropriate binding force sufficiently enough for stabilizing and supporting the patient interface, preventing an overly large pressure around the nostrils and the face of the patient. Because the two side extension arms are abutted against the upper positions of the cheekbones on the face, the pressure resulted by the overall weight of the mask is dispersed, at the same time preventing overly large compression on the philtrum and the upper lip of the wearer and further enhancing wearing comfort. Moreover, when the patient sleeps sideways, the frame and the headgear are unlikely pressed and thus unlikely deformed or shifted, thereby ensuring treatment effects of the patient wearing the patient interface.

DETAILED DESCRIPTION OF THE EMBODIMENTS

Objectives, features, and advantages of the present disclosure are hereunder illustrated with specific embodiments, depicted with drawings, and described below.

In the disclosure, descriptive terms such as "include, comprise, have" or other similar terms are not for merely limiting the essential elements listed in the disclosure, but can include other elements that are not explicitly listed and are however usually inherent in the units, components, structures, devices, modules, systems, portions, sections or regions.

In the disclosure, the terms similar to ordinals such as "first" or "second" described are for distinguishing or referring to associated identical or similar components or structures, and do not necessarily imply the orders of these components, structures, portions, sections or regions in a spatial aspect. It should be understood that, in some situations or configurations, the ordinal terms could be interchangeably used without affecting the implementation of the present invention.

In the disclosure, descriptive terms such as "a" or "one" are used to describe the unit, component, structure, device, module, system, portion, section or region, and are for illustration purposes and providing generic meaning to the scope of the present invention. Therefore, unless otherwise explicitly specified, such description should be understood as including one or at least one, and a singular number also includes a plural number.

The main embodiments of the present invention disclose a patient interface. The patient interface is used as a connection means for an airflow generated by a fluid generator to an airway of a patient (or other individual wearing the patient interface) to further construct a treatment system. A fluid generator can apply a treatment pressure to a part such as an airway of a patient or an entrance of an airway of a patient, wherein the entrance of an airway of the patient includes at least, for example, a nasal entrance and/or an oral entrance. The treatment pressure is defined as a continuous positive pressure relative to an atmospheric pressure where a patient is located, and is, for example, a continuous positive pressure between a pressure range of 2 to 40 cmH$_2$O. The treatment pressure is capable of improving a situation of breathing disorders caused by such as sleep breathing disorders of a patient. The patient interface disclosed by the present invention may also coordinate with another fluid generator, which can be used to deliver supplemental gas to the airway of the patient or to the entrance to the airway of the patient, for example, gas within a range of 0 to 6 liters per minute, or gas within a range of 30 to 70 liters per minute, provided to a patient capable of spontaneous breathing but requiring supplemental air.

Figure 1:
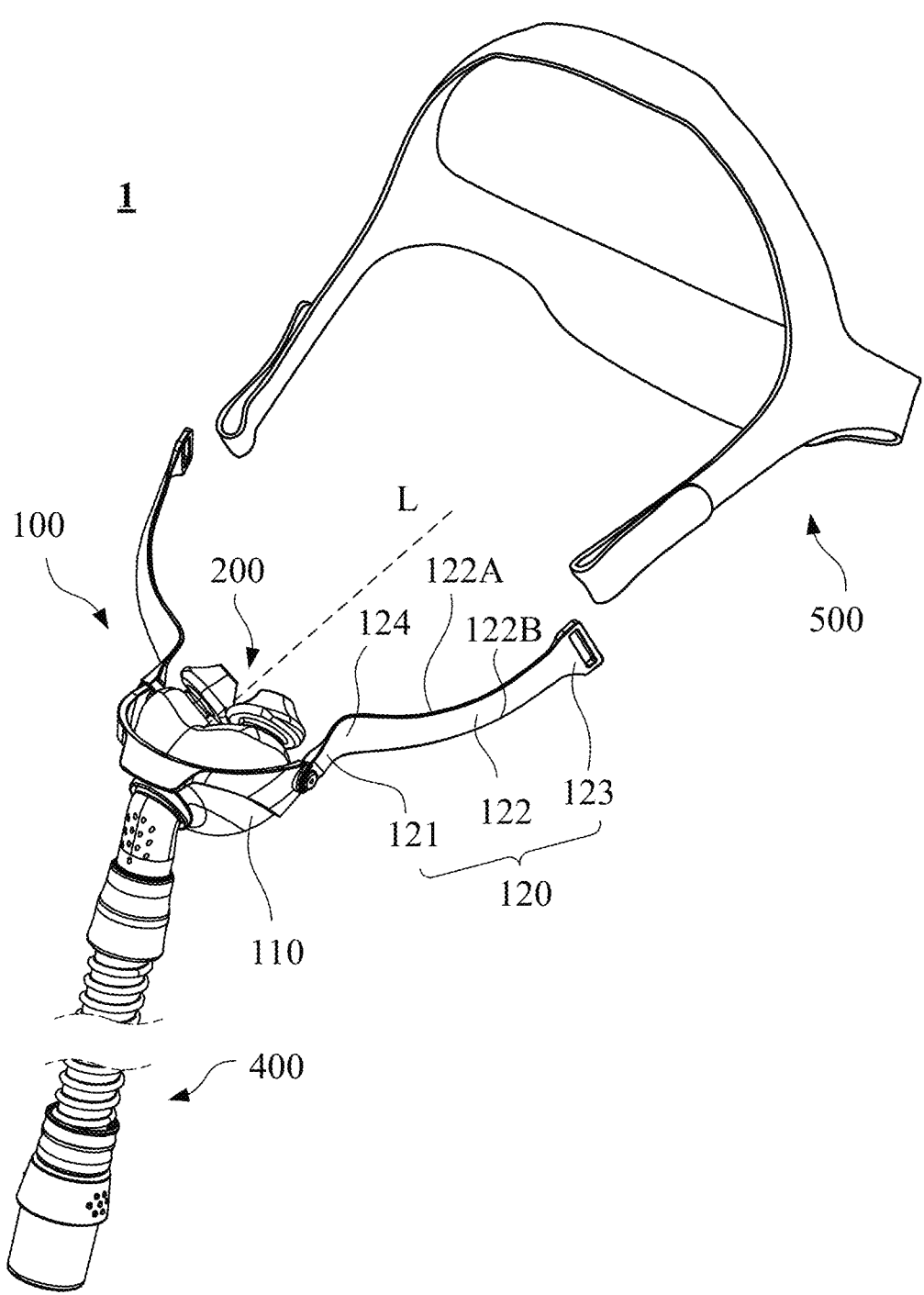
FIG. 1 is a structural schematic diagram of a patient interface according to an embodiment.
Figure 2:
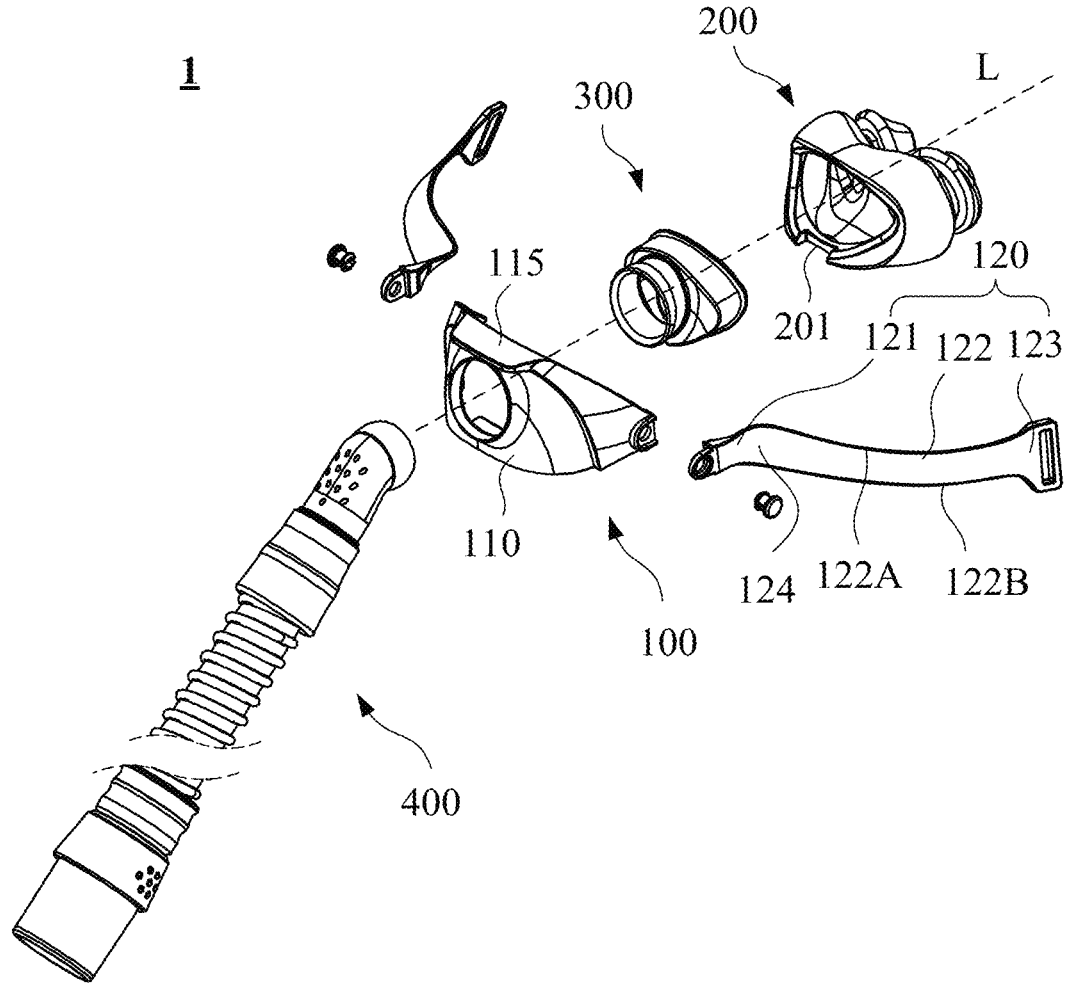
FIG. 2 is an exploded schematic diagram of a patient interface according to an embodiment.
Figure 3:
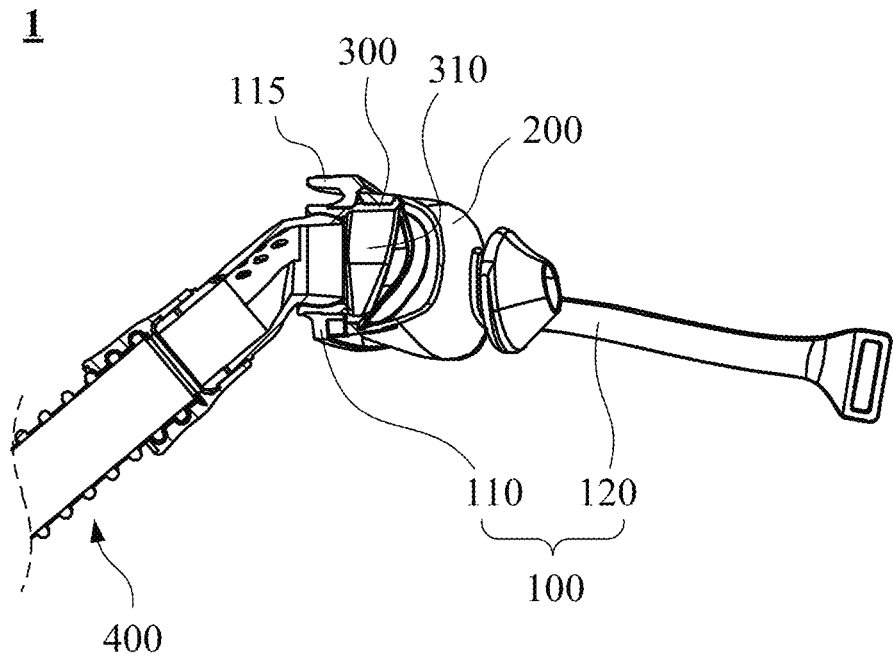
FIG. 3 is a section schematic diagram of a patient interface according to an embodiment.

Refer to FIGS. 1 to 3 showing a structural schematic diagram, an exploded schematic diagram and a section schematic diagram of a patient interface according to an embodiment of the present invention.

A patient interface 1 of this embodiment is exemplified by a nasal pillow patient interface. The patient interface 1 includes a frame assembly 100, a cushion assembly 200, an adaptor member 300, an elbow assembly 400 and a headgear 500. The frame assembly 100, the cushion assembly 200 and the elbow assembly 400 are individually attached to the adaptor member 300 and are further assembled together. Preferably, the elbow assembly 400 may not be in substantial direct contact with the frame assembly 100. Preferably, one end of the adaptor member 300 connected to the cushion assembly 200 has a passage opening 310. The passage opening 310 is for passing and delivering an airflow generated from a fluid generator (not shown) to the cushion assembly 200, and the width of the passage opening 310 is substantially equal to the height of the opening. The frame assembly 100 may be used to connect to the headgear 500 to stably maintain the patient interface 1 on an appropriate position of the head of the patient. Meanwhile, the cushion assembly 200 corresponds to the position of the nose of the patient, further creating a positive pressure environment near the nostrils for supplying breathing air. The patient interface of this embodiment is exemplified by a nasal pillow mask, and the cushion assembly 200 is correspondingly exemplified by a nasal pillow. The nasal pillow may be, for example but not limited to, sealed in the nostrils of the patient, or sealed near the nostrils of the patient. The patient interface may also be a nasal cover mask or a full cover mask, for example, a nasal cradle mask that does not seal the nose bridge but seals near the nostrils, or may be a high-flow nasal cannula inserted into the nostrils of the patient but does not seal the nostrils.

Figure 4:
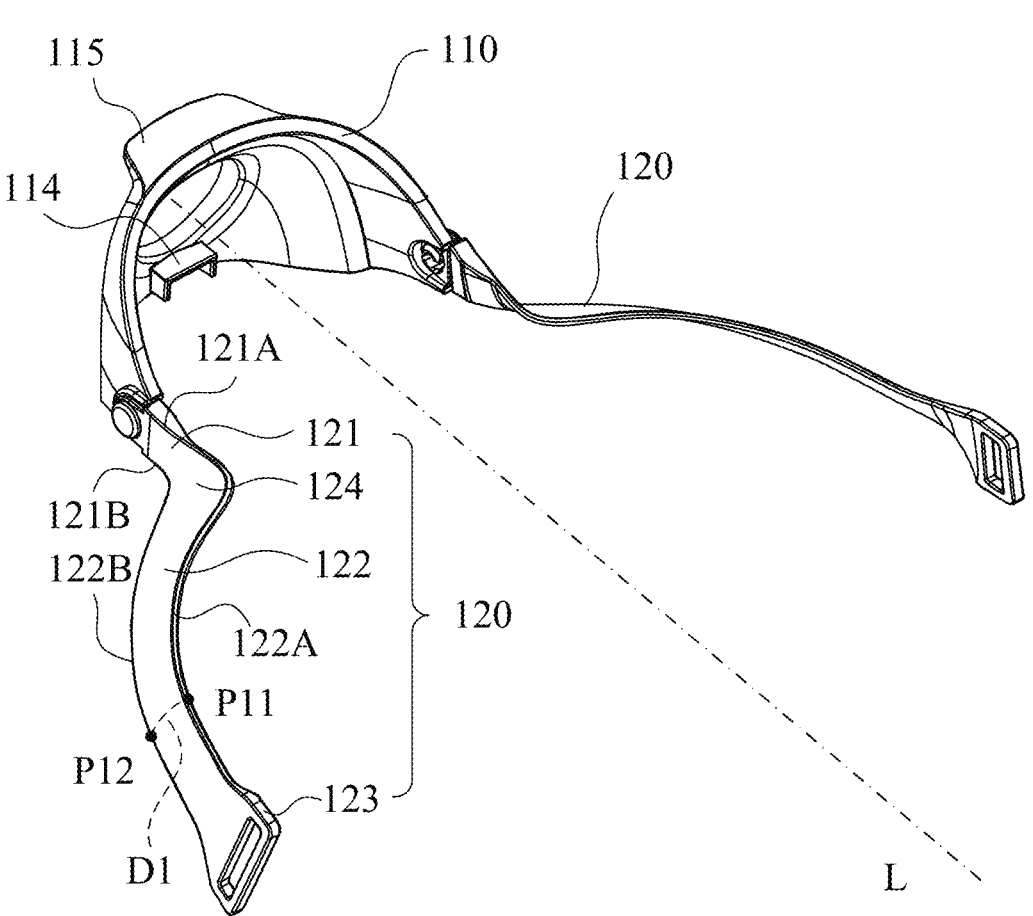
FIG. 4 is a structural schematic diagram of a frame assembly of a patient interface according to an embodiment.

Referring to FIG. 4, FIG. 4 shows a structural schematic diagram of a frame assembly of a patient interface according to an embodiment of the present invention. The frame assembly 100 has a main frame 110 and two side extension arms 120. The main frame 110 has a certain degree of rigidity, and is a frame made of, for example, polycarbonate (PC), so as to support the cushion assembly 200 having a lower hardness of the frame during wearing. Each of the side extension arms 120 extends from each of two sides of the main frame 110, and may be divided into a frame connecting section 121, a cheek contact section 122 and a headgear connecting section 123. One end of the frame connecting section 121 is rotatably or fixedly attached to the main frame 110. The cheek contact section 122 is abutted against the face of the patient during wearing. The headgear connecting section 123 is for connecting to the headgear 500. In a preferred embodiment, the headgear connecting section 123 is, for example but not limited to, an elongated narrow hole.

The side extension arm 120 has a rigidity smaller than that of the main frame 110 and is flexible, and is, for example, a flat sheet made of a thermoplastic polyester elastomer (TPEE) material, so that the two side arms 120 can be more easily everted outward or turned to facilitate an operation of wearing on the face of the patient. It should be noted that, there are no substantial direction differences in the degrees by which the two side extension arms 120 are everted outward or turned, and this advantage allows the two side extension arms 120 to more suitably comply with the facial shape near the upper halves of the cheekbones (i.e., zygomatic bone) of the patient with respect to head shapes or skull feature distributions of different human races, thereby providing better adjustability and ease of use. To increase comfort of the patient, the side extension arm 120 may be sleeved in a fabric sleeve (not shown), or a flexible material is arranged between the face of the patient and one side of the cheek contact section 122 close to the face of the patient, for example, a soft cushion, a gel or a breathable and moisture-permeable foam.

Figure 5:
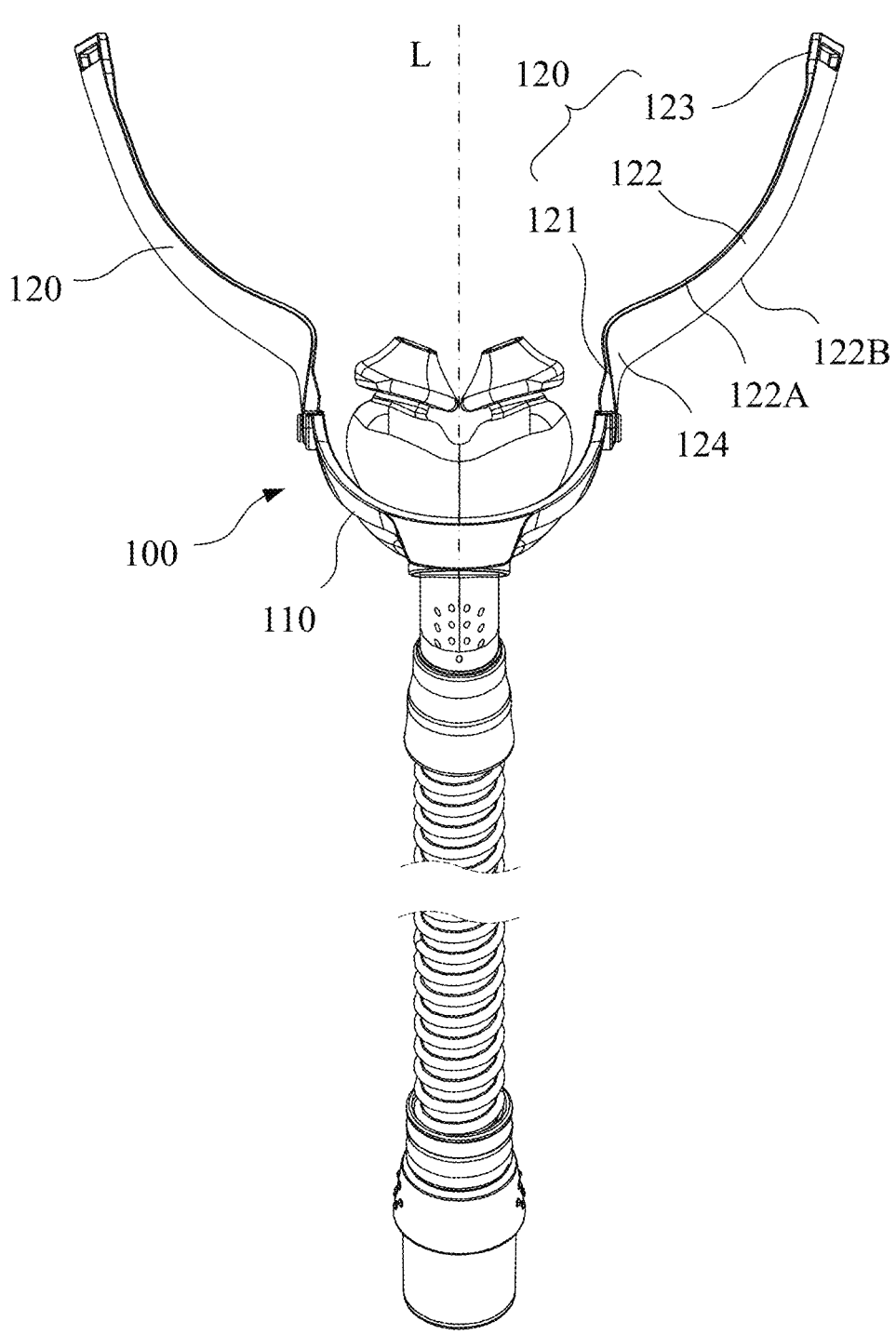
FIG. 5 is a top schematic diagram of a patient interface according to an embodiment.

As shown in FIG. 4 to FIG. 7, the cheek contact section 122 has an arc and a body that basically conforms to the cheek shape near the upper half of the cheekbone of the patient, and is in a substantially flat shape. The cheek contact section 122 has an upper edge 122A and a lower edge 1228, wherein the curvature of the lower edge 122B is smaller than the curvature of the lower edge 122B. As shown in FIGS. 2, 4 and 5, the patient interface 1 is defined with a mask central axis L, which is defined as a virtual extension line that passes through the center of an air inlet of the elbow assembly 400 and the center of an installation hole of the adaptor member 300. In this embodiment, when the side extension arm 120 does not receive a force, the upper edge 122A of the cheek contact section 122 is closer to the mask central axis L than the lower edge 1228 of the cheek contact section 122. As shown in FIG. 4, comparing a reference point P11 on the upper edge 122A and another reference point P12 at a corresponding shortest distance D1 on the lower edge 1228 along a surface of the side extension arm 120, the reference point P11 is closer to the mask central axis L, such that the upper edge 122A of the cheek contact section 122 is away from an apex of the cheekbone of the patient when the patient interface 1 is worn.

Figure 6:
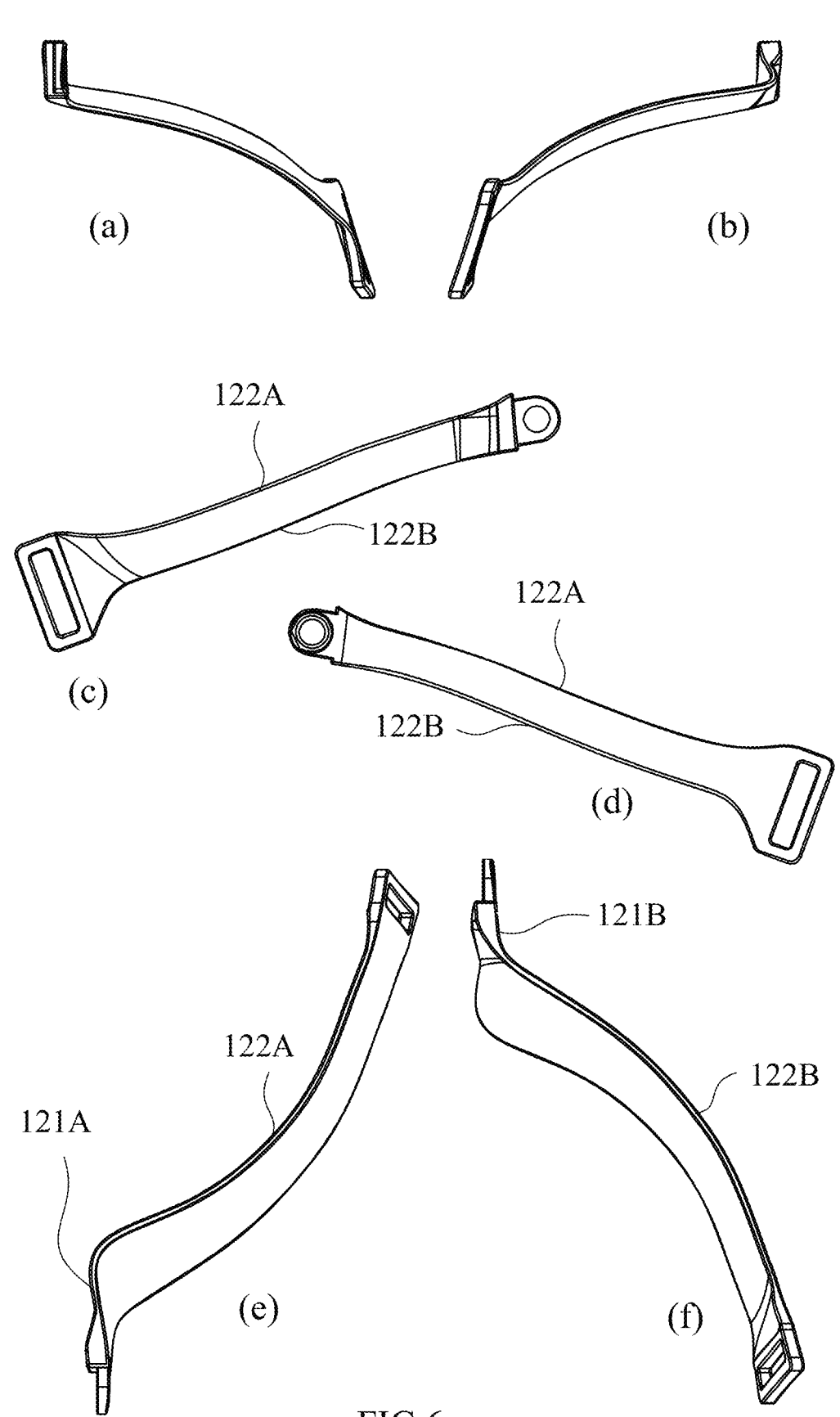
FIGS. 6(*a*) to 6(*f*) are views from six perspectives including a front view, a rear view, a left view, a right view, a top view and a bottom view of side extension arms according to an embodiment.
Figure 7:
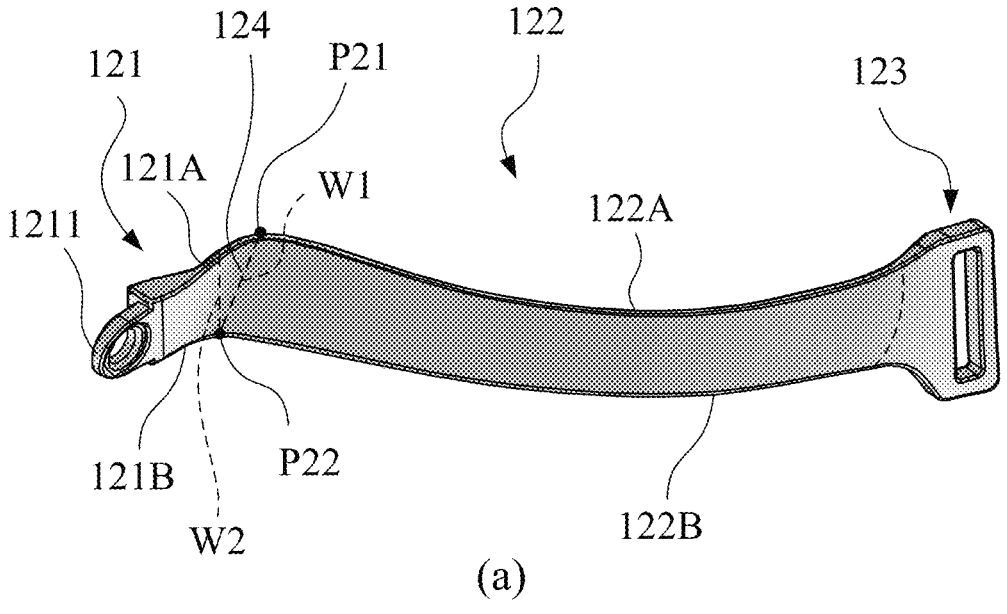
FIGS. 7(*a*) to 7(*e*) are schematic diagrams of a structure and a shape of a side extension arm of a patient interface according to an embodiment.
Figure 7:
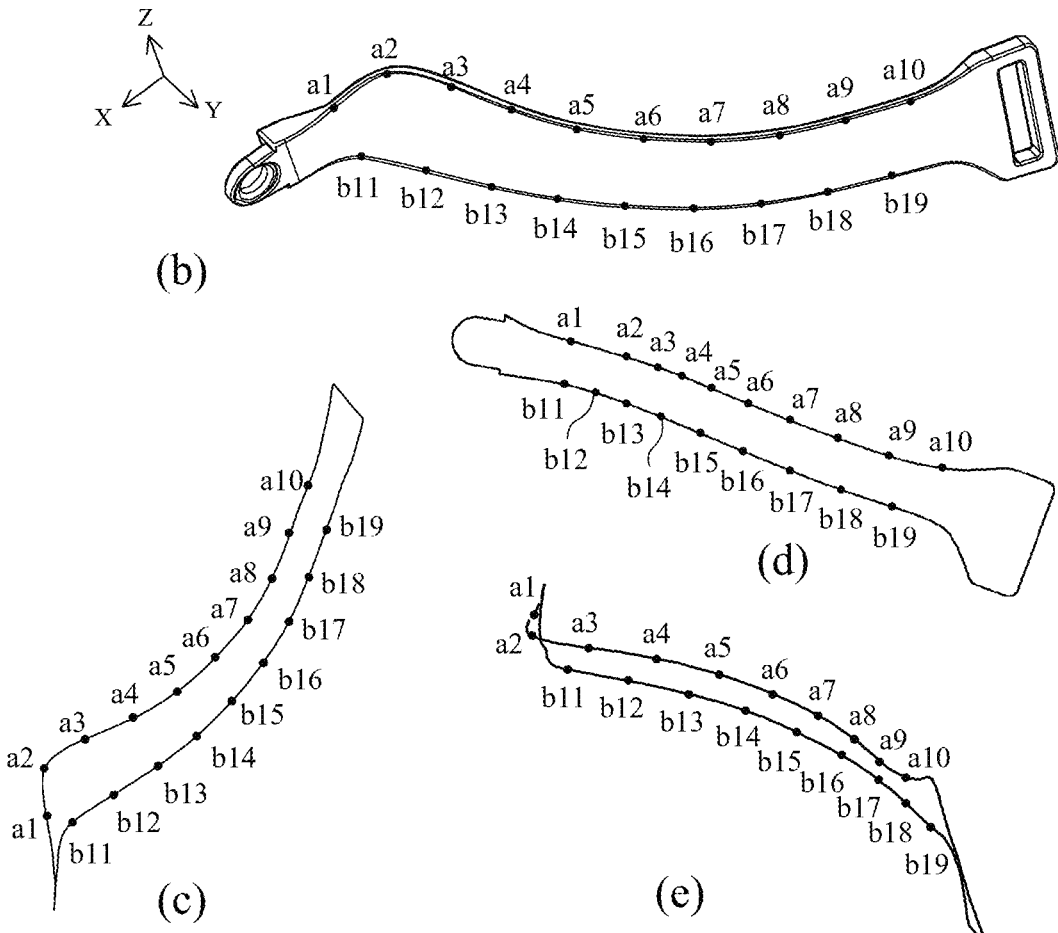

It should be noted that, the length of the distance D1 may gradually increase or gradually decrease in a direction closer to or farther away from the patient along the direction of the mask central line L. For example, the distance D1 corresponding a position with a largest change in curvature of the upper edge 122A may be the shortest, and the distance D1 of positions extending toward the two sides may gradually increase, and vice versa. As an example in this embodiment, a shortest distance between the upper edge 122A and the lower edge 1228 of the side extension arm 120 (alternatively speaking, a width of the cheek contact section 122 of the side extension arm 120) gradually increases in a direction as getting closer to the patient. As shown in FIG. 4 and FIG. 6, each side extension arm 120 has a first end close to a main frame 110 and a second end away from the main frame 110, and a shortest distance between the upper edge and 122A and the lower edge 1228 of the first end of the side extension arm 120 is smaller than a shortest distance between the upper edge 122A and the lower edge 122B of the second end. Thus, a contact area between the side extension arm 120 and the cheek of the patient increases as getting closer to the second end of the side extension arm 120. Thus, not only the stability of wearing the patient interface 1 is increased, but also wearing comfort is enhanced.

In this embodiment, a turning portion 124 is formed at a joint of the frame connecting section 121 and the cheek contacting section 124. The turning portion 124 is a part having a largest change in curvature on a side surface of a body of the side extension arm 120. When the patient interface 1 is not worn or when no force is received, the frame connecting section 121 extends from two sides of the main frame 122, and extension directions thereof are substantially parallel to the mask central axis L. The cheek contact section 122 extends along with the length, with the extension direction being away from the mask central axis L of the mask, until the headgear connecting section 123, and reaches the position farthest away from the mask central axis L.

As shown in FIGS. 7(a) to 7(e), in an example of the side extension arm in an outwardly everted form, a configuration in which the length of an upper edge 121A of the frame connecting section 121 is greater than the length of the length of a lower edge 121B is implemented, such that a connecting line between top and bottom apexes of the turning portion 124 is non-perpendicular to a tangent of the upper edge 121A or the lower edge 121B of the side extension arm 120. In other words, the turning portion 124 and the upper edge 121A (or the upper edge 122A of the cheek contact section 122) of the frame connecting section 121 are a meeting point P21, and the turning portion 24 and the lower edge 121B (or the lower edge 122B of the cheek contact section 122) of the frame connecting section 121 are a meeting point P22, wherein the meeting point P21 is distanced farther away from the joint (a front end side surface 1211) between the main frame 110 and the side extension arm 120 than the meeting point P22. On the other hand, the turning portion 124 has a width W1 greater than a width W2 of the frame connecting section 121, so as to form a result that the lower edge 122B of the cheek contact section 122 is farther away from the mask central axis L than the upper edge 122A. The change in curvature of the upper edge 122A of the cheek contact section 122 is also different from that of the lower edge 122B, with the curve of the lower edge 1228 being more moderate than the curve of the upper edge 122A. Moreover, when not affected by an external force, regarding a physical shape of the cheek contact section 122, a surface from the upper edge 122A extending to the lower edge 1228 is preferably a curved surface.

FIG. 7(b) depicts a plurality of reference points a1 to a10 and b11 to b19 labeled on the upper edge and the lower edge of the side extension arm 120. The reference points a1 to a10 are located in an equidistant distribution on the upper edge, and the reference points b11 to b19 are located in an equidistant distribution at the lower edge. FIGS. 7(c) to 7(e) show schematic diagrams of distributions of the reference points a1 to a10 and b11 to b19 on three projection planes (X-Y, X-Z and Y-Z) to provide better understanding for the shape of a body of the side extension arm 120 of this embodiment.

Figure 8:
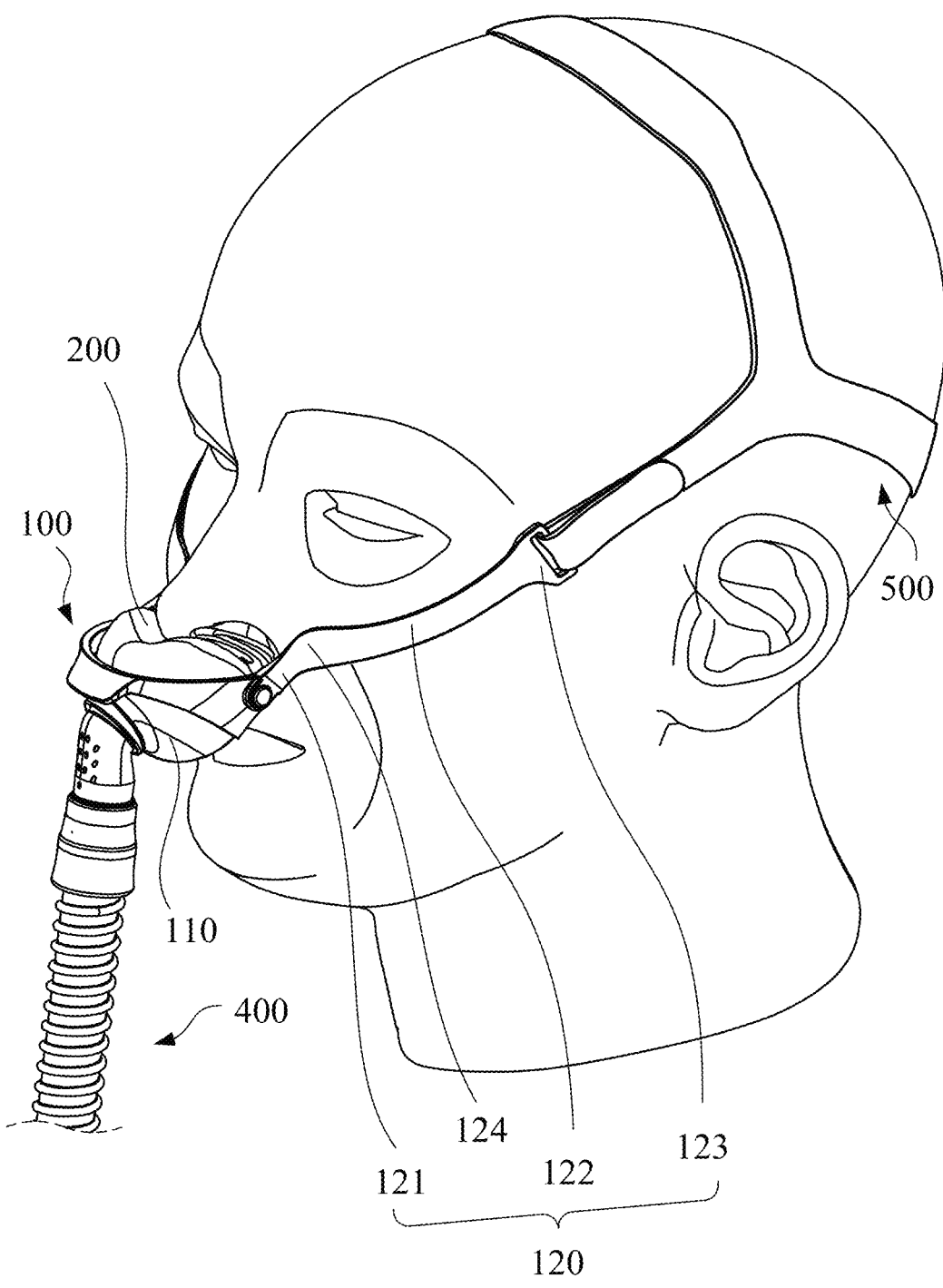
FIG. 8 is a schematic diagram of a patient interface being worn according to an embodiment.
Figure 9:
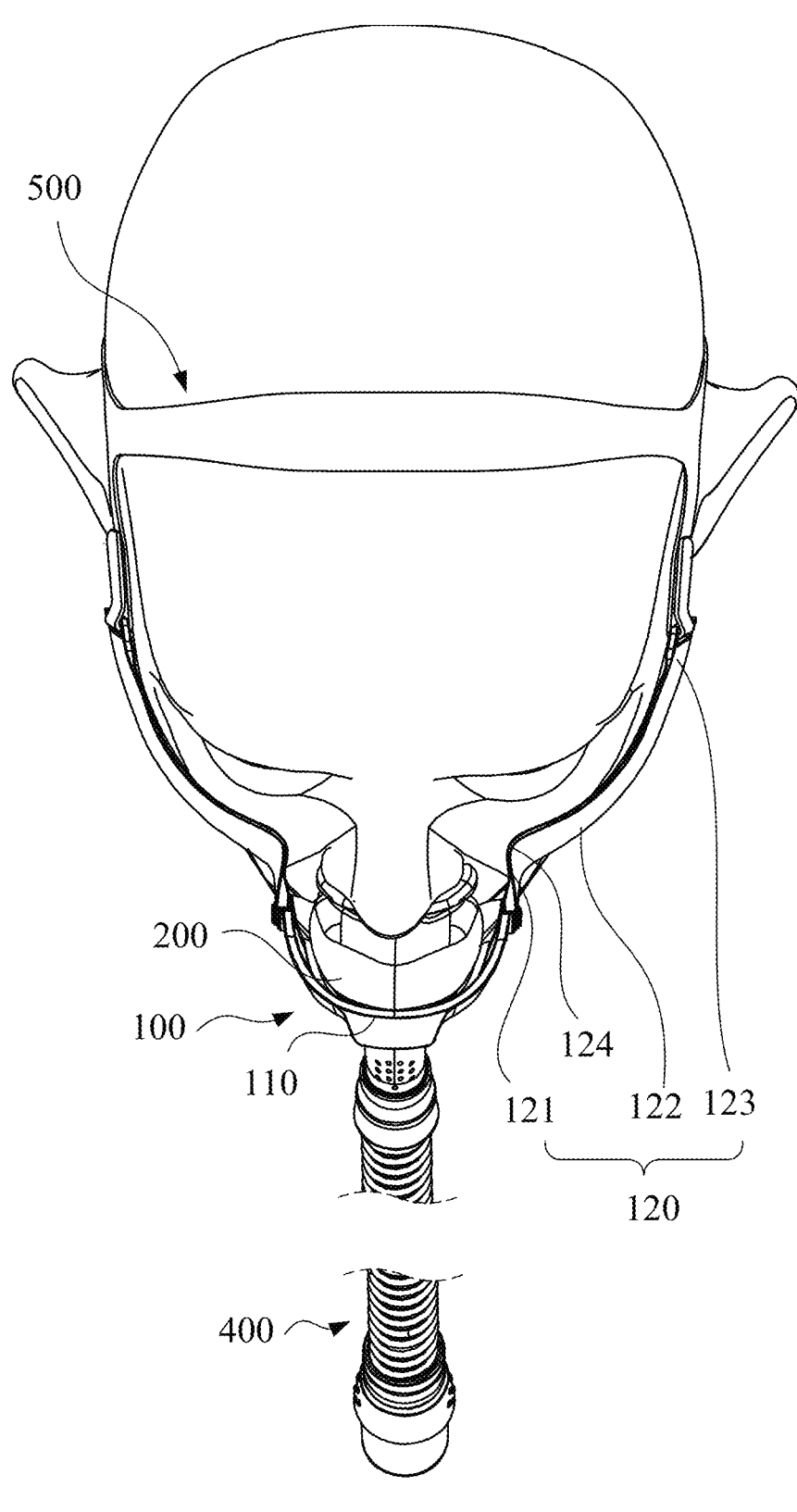
FIG. 9 is another schematic diagram of a patient interface being worn according to an embodiment.
Figure 10:
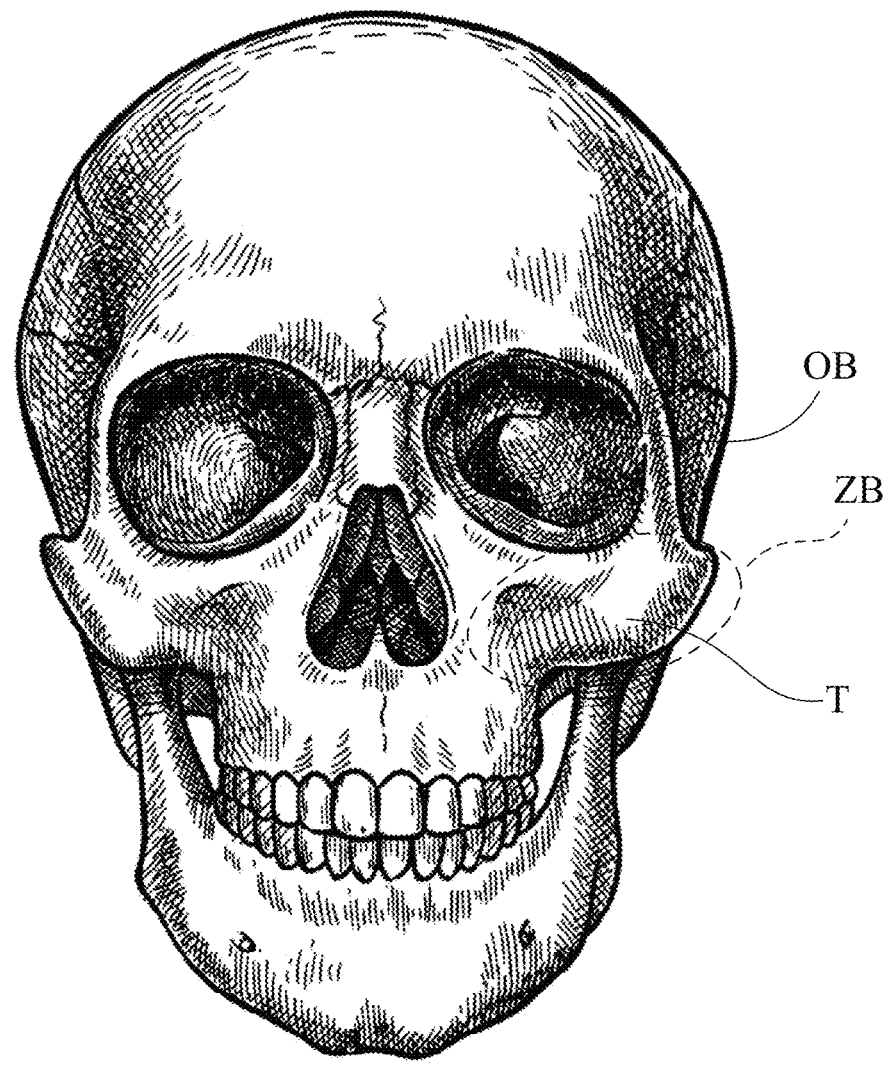
FIG. 10 is a schematic diagram of a human skull.

Referring to FIG. 8 to FIG. 10, FIG. 8 and FIG. 9 respectively show a perspective diagram and a top view when the patient interface of this embodiment is worn, and FIG. 10 shows a schematic diagram of a human skull.

When the patient interface of this embodiment is worn, the frame connecting section 121 of the side extension arm 120 substantially extends from a position connected to the main frame 110 toward the face of the patient by a shortest distance until the turning portion 124 near the nasal wing. The turning portion 124 supports near the nasal wing of the patient to increase the stability of the main frame 110. From the turning portion 124, the cheek contact sections 122 of the side extension arms 120 start to extend toward two sides of the face of the patient, and the cheek contact sections 122 have an outwardly everted form (for example, at least a portion folding in a direction toward the chin of the patient), so as to conform to the shape of the upper halves of the cheekbones on the face. The cheek contact section 122 is located between an apex T of a cheekbone ZB and an eye socket OB of the patient, and is still kept at an appropriate distance from the eye, so as to avoid eye discomfort or blocking of sight. The area of a surface on one side of the cheek contact section 122 close to the face of the patient is approximately 545 mm$^2$±10%. The cheek contact section 122 extends in a direction along the upper half of the cheekbone to between the temple to the corner of the eye, such that the headgear connecting section 123 is located at a position between the temple and the corner of the eye and is connected to the headgear 500.

The extension length of the frame connecting section 121 is associated with the depth by which the main frame 110 accommodates the cushion assembly 200 (a collapsible space of the cushion assembly 200 in main frame 110), a degree of hardness of the cushion assembly 200, a wearing angle of the cushion assembly 200 and a depth by which the head of the nasal pillow of the cushion assembly 200 enters the nostrils. In this preferred embodiment, the cushion assembly 200 is made of a silicon material, and includes a base and two nasal pillows in air communication with the base. Each nasal pillow includes a head and a neck. The head is a truncated hollow cone, and one end of the neck is connected to the base and the other end is connected to the head. In other preferred embodiments, the cushion assembly further includes two support portions, and the support portions are respectively located on outer sides of the two nasal pillows to abut against two sides of the nasal wings, for example, against nasolabial folds near the nasal wings. Moreover, at least a portion of the support portion is connected to the head of the nasal pillow, and the neck is located an on inner side of the nasal pillow. Thus, when the head of the nasal pillow is extended into the nostrils of the patient, the support portion can increase the wearing stability of the cushion assembly, and the neck of the nasal pillow can change an included angle between the heads of the two nasal pillows so as to reduce the pressure of the nasal pillows upon the nostrils. In another preferred embodiment, the cushion assembly similarly has a base, two nasal pillows and two support portions. However, each nasal has only a head but is not provided with a neck. Moreover, one side of the head of the nasal pillow, for example, an outer side, is connected to the corresponding support portion, and the other side of the head of the nasal pillow, for example, an inner side, is directly connected to the base. The head of the nasal pillow forms a protruding skirt, which can extend into the nostrils or fit to an outer periphery of the nostrils of the patient, and can deform according to the nasal shape/angles of nostrils of different patients so to reduce the pressure of the nasal pillow on the nostrils.

As shown in FIG. 10, on the human skull, the cheek bone ZB is located below the eye socket OB, and is a part that protrudes with respect to a facial profile, and the apex T of the cheekbone ZB is a most protruding position of the cheekbone on the facial profile. Divided by the apex T of the cheekbone ZB, a region extending in a direction from the apex T toward the eye socket OB is defined as an upper half of the cheekbone or an upper position of the cheekbone, and a region extending in a direction from the apex T toward the cheek is defined as a lower half of the cheekbone or a lower position of the cheekbone. Referring to FIGS. 8 to 10, when the patient interface of this embodiment is worn, the upper edge 122A of the cheek contact section 122 is closer to the eye socket OB of the patient than the lower edge 122B, thus forming an outwardly everted form of the side extension arm 120 that folds in a direction toward the chin of the patient, hence enabling the cheek contact section 122 to comply with the facial surface corresponding to the upper position of the cheekbone ZB.

A sagittal plane is anatomically defined as a longitudinal section that divides the human body into left and right parts, and a sagittal plane that divides a body trunk into left and right equal or symmetrical parts through the middle line of the body is defined as the median sagittal plane. When the patient interface of this embodiment is worn normally or in a normal condition, the mask central axis L is located on the median sagittal plane that equally divides the skull into left and right parts. Accordingly, when the patient interface of this embodiment is worn, the upper edge 122A of the cheek contact section 122 is closer to the median sagittal plane of the patient than the lower edge 122B, thus forming the outwardly everted form of the side extension arm 120.

The patient interface of this embodiment can be adhered to the facial surface corresponding to the upper halves of the left and right cheekbones ZB by the two side extension arms 120 having an outwardly everted shape. In particular, the cheek contact section 122 is abutted against on the upper position of the cheekbone between the apex T of the cheekbone ZB and the eye socket OB and away from the lower position of the cheekbone, and both the upper edge 122A and the lower edge 122B of the cheek contact section 122 are higher than the apex T of the cheekbone ZB, such that the overall weight of the patient interface can be transferred to the cheekbone ZB through the side extension arm 120. Compared to a method of securing the frame or the headgear at the apex T or the lower position of the cheekbone ZB and requiring pulling of the headgear or the use of a highly stretchable headgear to form an intense binding force for the frame or the headgear to stably clamp the head of the patient, the side extension arm 120 of this embodiment can be more effectively supported by an existing structure on the upper half of the cheekbone ZB, instead of having the frame or the headgear being pressed at the apex T or the lower half of the cheekbone ZB purely by the binding force of the headgear, so that the patient interface can be further prevented from sliding downward. Thus, without requiring the patient to pull the headgear overly tight or to use a highly stretchable headgear, the patient interface can be stably secured on an appropriate position on the face, thereby preventing the patient interface from producing an overly large compression around the nostrils and cheeks of the patient.

Moreover, the side extension arm 120 corresponds to the position of the upper half of the cheekbone ZB when the patient interface is worn, it avoids the apex T of the cheekbone ZB that is most protruding on the face, and is not located on the lower position of the cheekbone that comes into contact with the pillow when the patient sleeps sideways. Thus, when the patient wearing the patient interface of this embodiment sleeps sideways, discomfort due to excessive compression of the side extension arm 120 on the face is less likely caused. This reduced sensation of a foreign object of the patient interface is beneficial for promoting compliance of the patient.

Since each side extension arm 120 is a flat sheet made of a flexible material and can be easily be everted outward or turned in response to the change in the facial shape of the patient, the cheek contact sections 122 of the side extension arms 120 can better comply with the profile of the upper halves of the left and right cheekbones to disperse the weight of the patient interface on the cheekbones, so as to prevent the mask from drooping excessively due to gravity, further reducing discomfort caused by excessive pressure of the cushion or nasal pillows on the face and upper lip of the patient. The flexible material may be selected from, for example but not limited to, a thermal plastic material (for example, TPEE), a polymer material, an adhesive or a foam material, or a composite material including any of the above.

As shown in FIG. 8 and FIG. 9, the length of the cheek contact section 122 is greater than the length of the frame connecting section 121 and the length of the headgear connecting section 123, such that each side extension arm 120 extends across the cheek of the patient during wearing, and the headgear connecting section 123 is substantially located on a position between the corner of the eye and the temple. With the connection of the headgear 500, the patient interface is maintained at a fixed position, and the two side extension arms 120 are kept on the upper positions of the cheekbones.

According to one embodiment of the present invention, the frame assembly 100 is configured such that each side extension arm 120 is rotatable, rotatable by a limited degree or non-rotatable relative to the main frame 110 on a plane parallel to the sagittal plane. If the side extension arm 120 is rotatable relative to the main frame 110, the angle between the side extension arm 120 and the main frame 110 is adjustable, allowing the side extension arm 120 to adapt to head shapes of a larger number of patients. If the side extension arm 120 is non-rotatable relative to the main frame 110, the overall stability of the patient interface can be increased.

Figure 11:
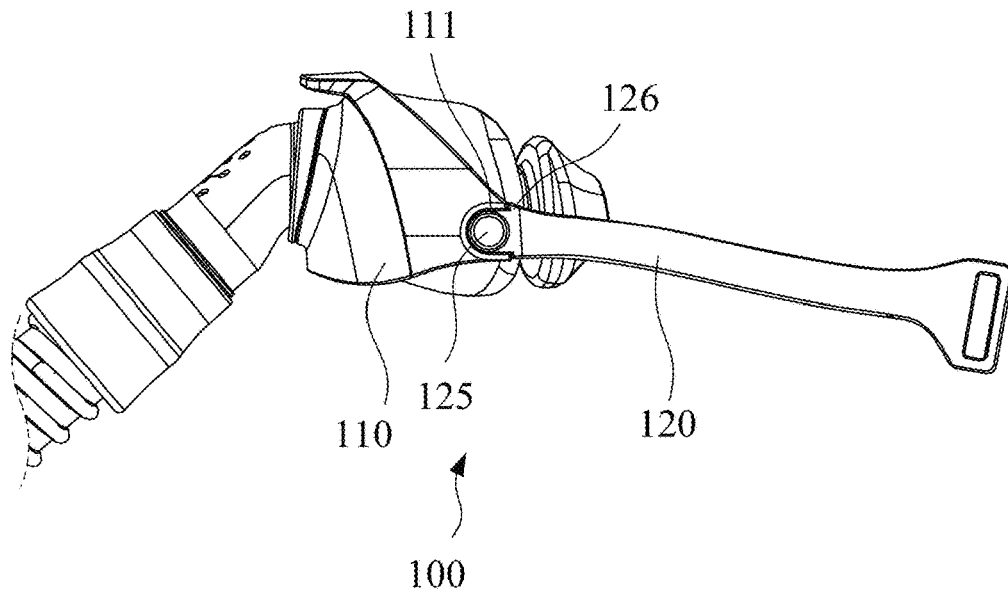
FIG. 11 is a side schematic diagram of a patient interface according to an embodiment.
Figure 12:
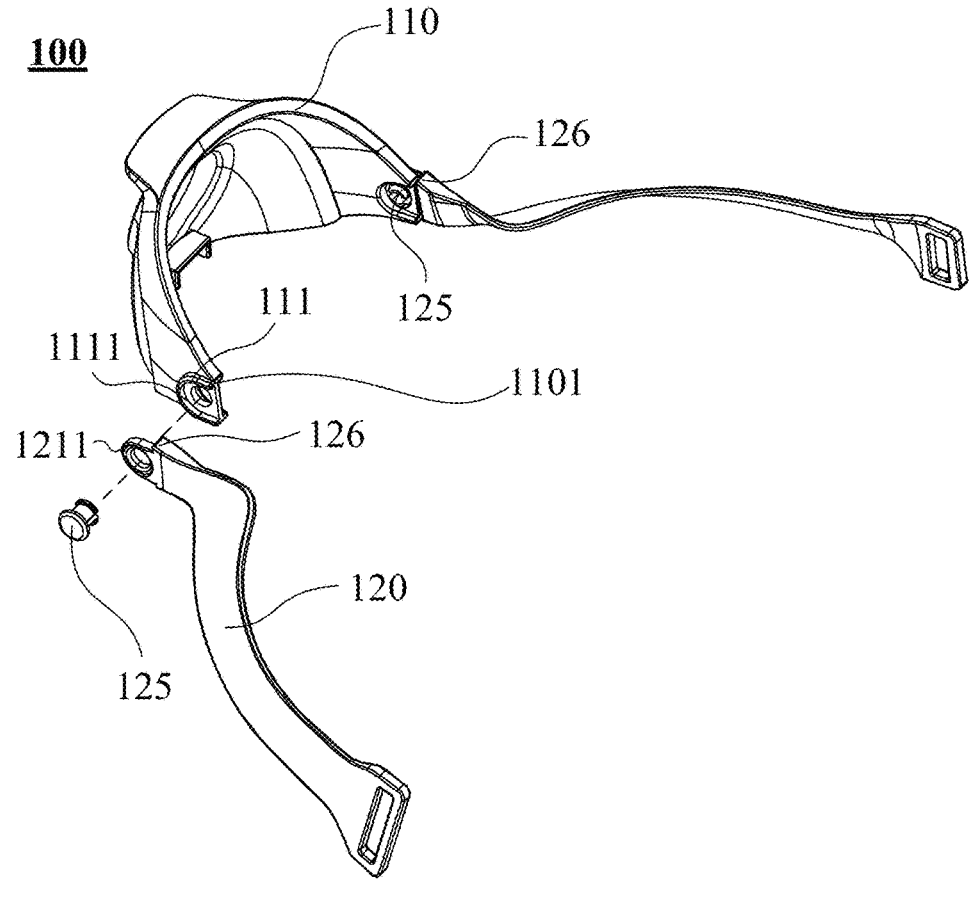
FIG. 12 is an exploded partial schematic diagram of a patient interface according to an embodiment.

Referring to FIGS. 11 and 12, the side extension arm 120 of this embodiment is incapable of swinging up and down relative to the main frame 110; that is, the side extension arm 120 is non-rotatable relative to the main frame 110 on a plane parallel to the sagittal plane.

For example, the frame connecting section 121 of each side extension arm 120 and the main frame 110 may be assembled together by a fastening structure 125. The fastening structure 125 may be a discrete coupling member, or may be a structure form integrally with the side extension arm 120 or the main frame 110—such is not specifically restricted by this embodiment of the drawings. In other embodiments, the frame connecting section 121 of each side extension arm 120 and the main frame 110 may be an integral.

The main frame 110 may be provided with a first limiting portion 111 on a position correspondingly connected to the side extension arm 120, so as to limit a rotatable range of the side extension arm 120 about the fastening structure 125 as an axis. As shown in FIGS. 11 and 12, the first limiting portion 111 is a stop wall protruding outward from a surface of the main frame 110, and has a concave opening formed complementary to the shape of the front end side surface of the frame connecting section 121 of the side extension arm 120. An inner sidewall 1111 of the first limiting portion 111 is abutted against the front end side surface 1211 of the frame connecting section 121 of the side extension arm 120, and limits the side extension arm 120.

The side extension arm 120 may have a second limiting portion 126, which is a stop block formed on the front end side surface (upper edge/lower edge) of the frame connecting section 121, so as to abut against the main frame 110 and an end surface 1101 of the first limiting portion 111, further forming interference between the second limiting portion 126 and the main frame 110 to upward or downward swing. In this embodiment, a surface of the second limiting portion 126 for abutment is substantially parallel to the end surface of the first limiting portion 111.

According to this embodiment, the limiting effect can be achieved by implementing at least one of the first limiting portion 111 and the second limiting portion 126.

Figure 13:
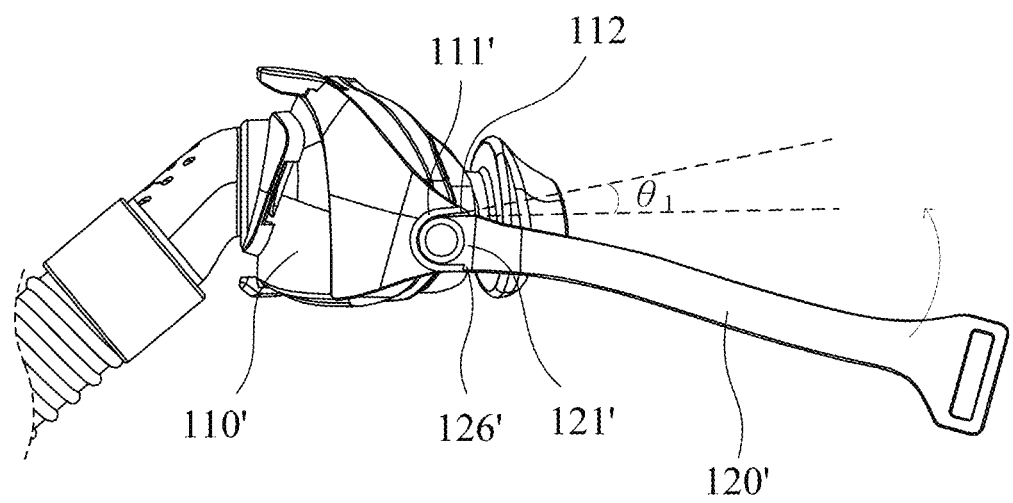
FIG. 13 is a side schematic diagram of a patient interface according to another embodiment.

Referring to FIG. 13, a side extension arm 120' of this embodiment is capable of swinging upward relative to a main frame 110' within a limited angle range.

As shown, a gap 112 is present between a first limiting portion 111' and a frame connecting section 121' of the side extension arm 120'; that is, the shape of the concave opening formed by the first limiting portion 111' is not exactly complementary to the shape of a front end side surface of the frame connecting section 121' of the side extension arm 120'. Thus, the side extension arm 120' is capable of swinging upward within a range of an angle $\theta_1$, which may be 3 to 5 degrees.

In this embodiment, a second limiting portion 126' is configured on a lower edge of the frame connecting section 121' of the side extension arm 120', so as to allow the side extension arm 120' to swing only upward.

Figure 14:
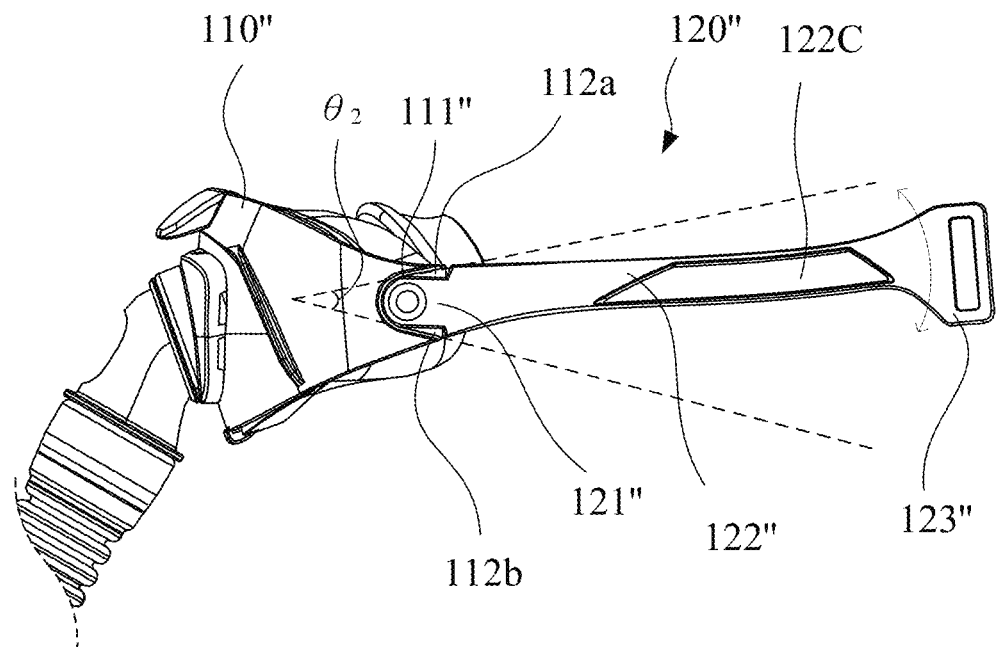
FIG. 14 is a side schematic diagram of a patient interface according to another embodiment.

Referring to FIG. 14, a side extension arm 120" of this embodiment is capable of swinging upward and downward relative to a main frame 110" within a limited angle range.

As shown, gaps 112a and 112b are present between a first limiting portion 111" and a frame connecting section 121" of the side extension arm 120"; that is, the shape of the concave opening formed by the first limiting portion 111" is complementary by even a lesser part to the shape of a front end side surface of the frame connecting section 121" of the side extension arm 120". Thus, the side extension arm 120" is capable of swinging upward and downward within a range of an angle $\theta_2$, which may be 1 to 26 degrees, and is preferably 22 to 25 degrees.

As an example, the thickness of a cheek contact section 122" may be between 0.5 to 1 mm, and is preferably 0.8 mm.

To reinforce stability, the overall thickness of partial thickness of the frame connecting section 121" for connecting the main frame 110" and the overall thickness or partial thickness of a headgear connecting section 123" for connecting the headgear are thicker than the thickness of the cheek contact section 122". The longer and thinner cheek contact section 122" provides the side extension arm 120" with flexibility for the two side extension arms 120" to open outward when wearing is not fully performed, further forming a greater opening angle between the two side extension arms 120" to facilitate the wearing operation and to adapt to facial shapes of different sizes. Moreover, the thickness of the cheek contact section 122" may also be uniform or varying. For example, as shown in FIG. 14, the cheek contact section 122" may have a recessed portion 122C so that the cheek contact section 122" has a smaller thickness at the recessed position, further increasing flexibility.

Figure 15:
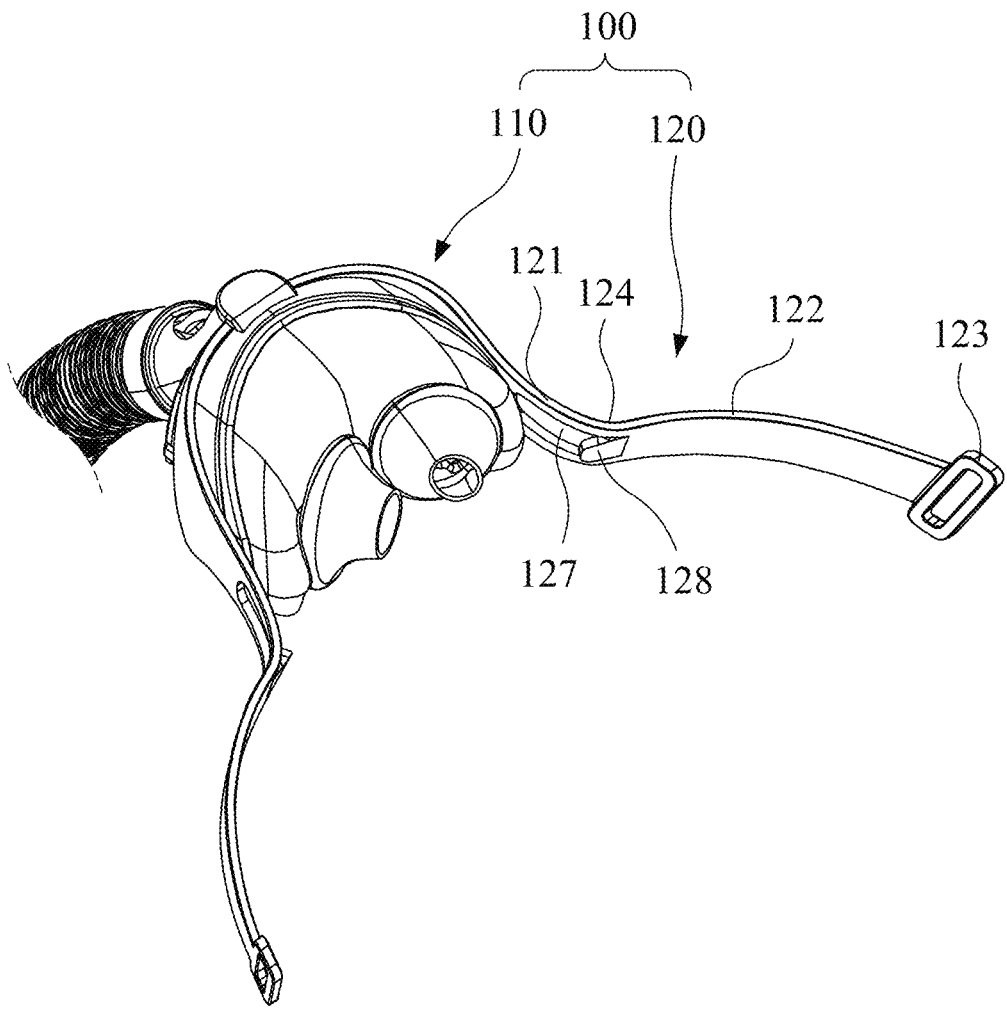
FIG. 15 is a side schematic diagram of a patient interface according to yet another embodiment.

As shown in FIG. 15, the side extension arm 120 may have an opening portion 127. The opening portion 127 may be formed on a position of the turning portion 124 or a position near the turning portion 124, so as to enhance the flexibility of the side extension arm 120, which can more easily flex outward (away from the mask central axis L) or inward (toward the mask central axis L). In an alternative embodiment, the opening portion may be located only within the frame connecting section, and is not limited to the example in the drawings.

Moreover, the side extension arm 120 may be provided with a sheet 128 on the position of the turning portion 124. The sheet 128 extends from the cheek contact section 122 and protrudes in the opening portion 127. The sheet 128 is connected to the cheek contact section 122 so as to form together with the cheek contact section 12 a surface that contacts the cheek, thereby increasing the area by which the side extension arm 120 contacts the face. The thickness of the sheet 128 may be equal to the thickness of the cheek contact section 122. In addition, the sheet 128 extends from the cheek contact section 122 and protrudes in the opening portion 127 and thus forms a hook structure on the position of the turning portion 124. When the patient needs to sleeve the side extension arm 120 by a fabric sleeve (not shown), one end of the fabric sleeve may be hooked on the hook structure formed by the sheet 128 so that the fabric sleeve does not slide off easily.

Figure 16:
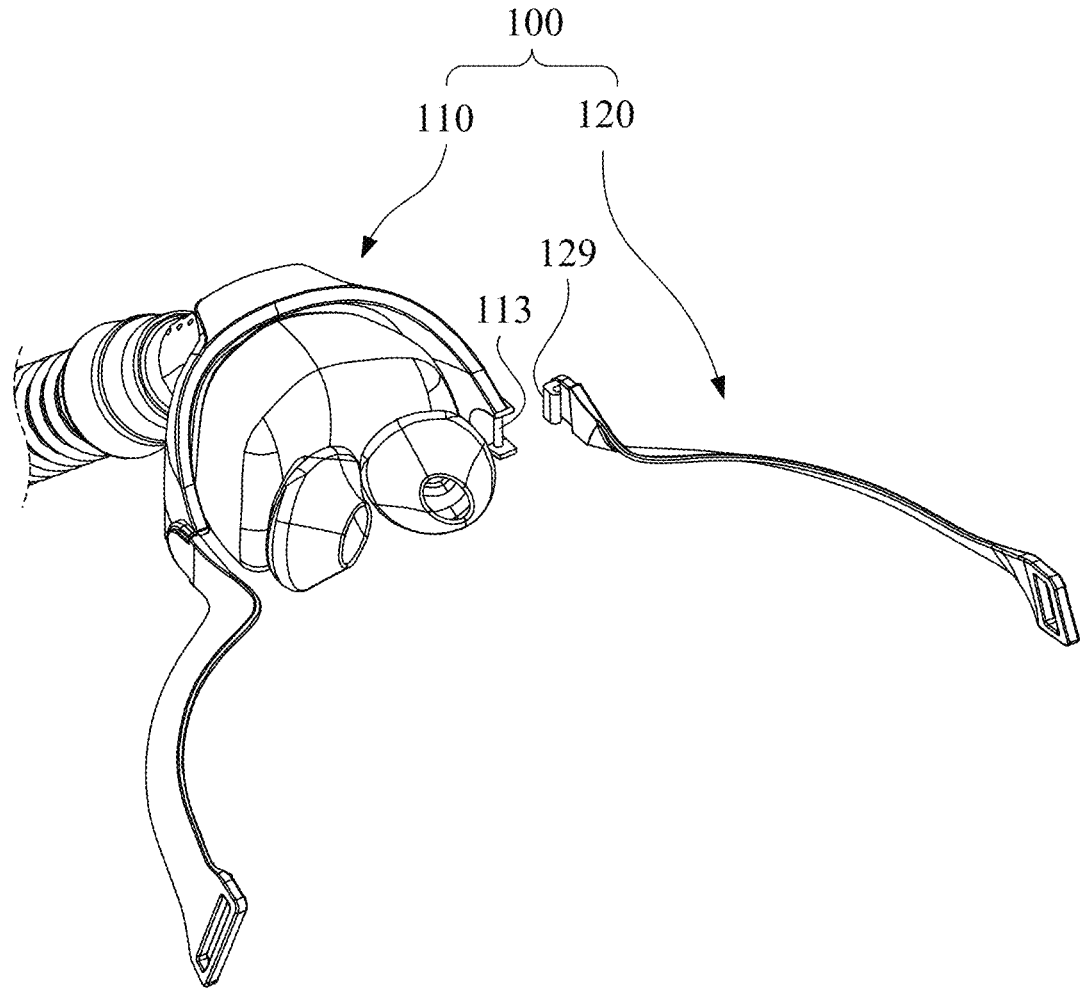
FIG. 16 is a side schematic diagram of a patient interface according to yet another embodiment.

Referring to FIG. 16 showing a structural schematic diagram of a patient interface according to another embodiment of the present invention. The frame assembly 100 may be configured such that, each side extension arm 120 is rotatable relative to the main frame 110 and opens outward, and a greater opening angle is formed between the two side extension arms 120, such that the side extension arms 120 can more easily flex outward (away from the mask central axis L) or inward (toward the mask central axis L).

For example, a rotation pin 113 is provided on each of left and right sides of the main frame 110, and a fastener 129 is provided on a front end of the frame connecting section 121 of the side extension arm 120. The fastener 129 correspondingly fastens on the rotation pin 113, allowing the side extension arm 120 to rotate about the rotation pin 113 as an axis and be opened outward.

Figures 17, 18:
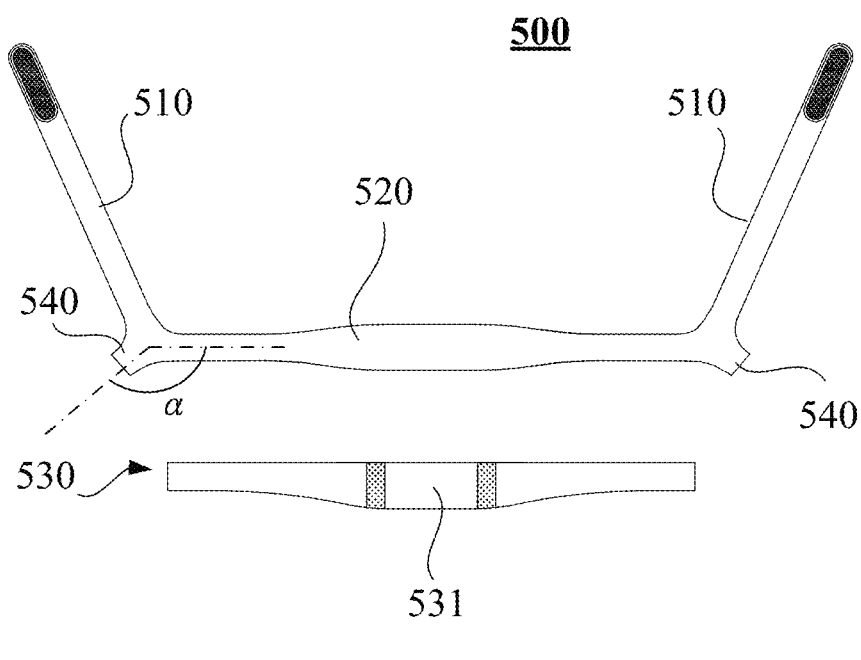
FIG. 17 is a schematic diagram of a patient interface in which a headgear is not yet combined according to an embodiment.
FIG. 18 is a schematic diagram of a patient interface in which a headgear is combined according to an embodiment.

Referring to FIGS. 17 and 18 as well as FIGS. 1, 8 and 9, FIG. 17 shows a schematic diagram of the patient interface in which the headgear 500 is not yet combined according to an embodiment, and FIG. 18 shows a schematic diagram of the patient interface in which the headgear 500 is combined according to an embodiment.

According to an embodiment of the present invention, the headgear 500 may include a plurality of straps. These straps are for adjusting the position of the patient interface when the patient interface is worn by the patient, allowing the patient interface to be stably and comfortably secured at the head of the patient, and to form an airflow space, breathing chamber or inflating chamber on the face of the patient, so as to apply a treatment pressure to the airway of the patient. These straps at least include two side straps 510, a top strap 520 and a back strap 530. The top strap 520 is connected between the two side straps 510, and each of the side straps 510 is for detachably attaching to the headgear connecting section 123 of the side connecting arm 120 of the corresponding side. The side strap 510 may pass through a connection hole on the headgear connecting section 123, and may be secured by a hook-and-loop structure or a button or by other means. The two side straps 510 and the top strap 520 may be an integral, a connecting portion 540 (one on each of left and right sides) is provided on a connecting position of the side strap 510 and the top strap 520, and the connecting portion 540 is for joining with the back strap 530 by means of, for example, sewing. When the patient interface is worn, the top strap 520 crosses over the head of the patient, and the back strap 530 is located on a position of the occipital bone of the patient.

In this embodiment, an elastic section 531 may be provided in the middle of the back strap 530. The elastic section 531 may be a flexible woven strap made of a blended material of nylon and spandex. Other parts of the back strap 530 may be made of a composite fabric implemented by a combination of fabric and foam, so that the back strap 530 has sufficient support and does not warp easily. On the back strap 530, the elasticity of the elastic section 531 is greater than those of the other parts. During wearing, the elastic section 531 is elastically expandable to conform to the shape of the occipital bone of the head of the patient.

As an example, the elongation rate of the elastic section 531 is 200%, and the elongation rate of other parts of the back strap 530 is 100%.

As an example, a ratio of the length of the elastic section 531 to the total length of the back strap 530 may be between 8.77% and 26.32%. Preferably, the ratio of the length of the elastic section 531 to the total length of the back strap 530 may be 17.54%. In practice, the length of the elastic section 531 may be 40 mm, and the length of the back strap 530 may be 228 mm.

The width of the back strap 530 and the width of the elastic section 531 may be equal or different. For example, the width of the back strap 530 is wider in the middle and narrower on two sides, and the width of the elastic section 531 is the widest. A ratio of the narrower ends of the back strap 530 to the total width of the elastic section 531 may be between 52% and 68%. Preferably, the ratio of the narrower ends of the back strap 530 to the total width of the elastic section 531 may be 60%. The width of the back strap 530 may continuously varying or discontinuously varying. With the design of the elastic section 531 having a wider width in the middle of the back strap 530 and a greater flexibility, the comfort and stability of wearing of the patient interface can be enhanced. In practice, the lengths of the narrower ends of the back strap 530 may be between 12 and 20 mm, and is preferably 12 mm±1 mm; the total width of the elastic section 531 is at least more than 15 mm, and is preferably 20 mm±1 mm.

The width of the top strap 520 may vary, or may be non-varying and kept constant. In this embodiment, the width of the top strap 520 is wider in the middle and narrow on two sides, and a ratio the width of the narrower two ends (positions closer to the connecting portions 540) to the total width of the widest part in the middle may be between 53% and 68%. Preferably, the ratio the width of the narrower two ends (positions closer to the connecting portions 540) to the total width of the widest part in the middle may be 60%. With the design of a wider width in the middle of the top strap 520, the stability of wearing of the patient interface can also be enhanced. In practice, the lengths of the narrower two ends of the top strap 520 may be between 12 and 20 mm, and is preferably 12 mm±1 mm; the length of the widest part in the middle of the top strap 520 may be at least more than 15 mm, and is preferably 20 mm±1 mm In this embodiment, once the back strap 530 is combined with the connecting portion 540, the back strap 530, the side straps 510 and the top strap 520 may form the headgear 500. The connecting portion 540 extends by a length from a joint of the side strap 510 and the top strap 520, an extension direction thereof is substantially parallel to the combined back strap 530, and the extension direction of the connecting portion 540 and the extension direction of the top strap 520 have a strap included angle α in between. The strap included angle α is an obtuse angle greater than 100 degrees and smaller than 180 degrees, and preferably, the strap included angle α is 150 degrees.

In continuation of the description above, to prevent the patient interface from inappropriate compression on the face and head of the patient, the two side extension arms of the patient interface of the present invention are located on the upper halves of the left and right cheekbones. In order to stably keep the side extension arms 120 on the upper halves of the cheekbones, the patient interface of the present invention can be applied with the coordination of the headgear 500, with at least a part of the headgear 500 being located near the occipital bone of the patient. For example, the top strap 520 of the headgear 500 is located at the parietal bone of the head of the patient, the back strap 530 of the headgear 500 is located at the occipital bone of the head of the patient, and an obtuse angle is kept between the extension direction of the connecting portion 540 of the headgear 500 and the extension direction of the top strap 520. Thus, the patient interface is prevented from sliding off from the direction of the top of the during sleeping of the patient, providing the overall patient interface with more stable wearing effects. However, due to different features of the occipital bones of the heads of different individuals, in order to have the back strap 530 conform to the shapes of the occipital bones of the heads of different patients, the elastic section 531 of the back strap 530 has a greater degree of elongation than the top strap 520, so as to ensure the overall balance on the head of the patient wearing the patient interface, and the issues of headgears in multiple sizes that need to be manufactured due to poor elongation of the headgear 500 can be solved at the same time.

Referring to FIG. 2 and FIG. 4, for the patient to easily identify an installation direction of the frame assembly 100 and the cushion assembly 200, a protrusion 114 is provided on one side of the main frame 110 close to the cushion assembly 200 to correspond to an indentation 201 of the cushion assembly 200. However, the present invention is not limited to the structure above, and shapes (for example, a triangle or a trapezoid), indication symbols or texts (for example, R for right and L for left) may also be used to provide indication prompts. Moreover, referring to FIGS. 1 to 4, for the patient to easily identify the direction for wearing the patient interface 1 in an environment with insufficient lighting, a sheet 115 is provided on an upper side of the main frame 110, and the sheet 115 protrudes in a direction away from the cushion assembly 200. Thus, without relying totally on the vision, the patient can perceive top/bottom/front/back directions of the patient interface 1 through the sense of touch so as to confirm the direction for wearing. The elbow assembly 400 of the patient interface 1 is usually rotatable relative to the frame assembly 100 so as to coordinate with a placement position of the CPAP respirator. Thus, for the patient to easily identify the direction for wearing the patient interface 1, the elbow assembly 400 may be designed to be rotatable by a limited angle relative to the frame assembly 100, for example, 180 degrees to 359 degrees; however, the present invention is not limited to the example above. With the rotation of the elbow assembly 400, the patient may also perceive the top/down directions of the patient interface 1, thereby determining the direction for wearing the patient interface 1.

Accordingly, the patient interface disclosed by the embodiments of the present invention has two downwardly and outwardly everted side extension arms so as to be closely comply with the upper halves of the cheekbones on the face, hence providing the patient interface with better support to prevent the mask from sliding down or drooping, and at the same time preventing excessive compression on the philtrum and the upper lip. Moreover, because the two side extension arms are abutted against the upper positions of the cheekbones on the cheeks, the pressure caused by the overall weight of the mask is dispersed, thus providing enhanced wearing comfort.

The present disclosure is illustrated by various aspects and embodiments. However, persons skilled in the art understand that the various aspects and embodiments are illustrative rather than restrictive of the scope of the present disclosure. After perusing this specification, persons skilled in the art may come up with other aspects and embodiments without departing from the scope of the present disclosure. All equivalent variations and replacements of the aspects and the embodiments must fall within the scope of the present disclosure. Therefore, the scope of the protection of rights of the present disclosure shall be defined by the appended claims.

What is claimed is:

1. A patient interface for delivering air to an airway of a patient, the patient interface comprising:
    a headgear, adapted to maintain the patient interface on a head of the patient; and
    a frame assembly, adapted to connect to the headgear, wherein, when worn, the frame assembly configured to abut against an upper position of a cheekbone of a cheek of the patient and is away from a lower position of the cheekbone of the cheek of the patient, the frame assembly having a main frame and two side extension arms, the two side extension arms respectively extending from two sides of the main frame, each of the two side extension arms including a single cheek contact section,
    wherein, when no force is applied to the side extension arm, an upper edge of the cheek contact section of the side extension arm is closer to a mask central axis of the patient interface than a lower edge of the cheek contact section, such that the upper edge and the lower edge of the cheek contact section are higher than an apex of the cheekbone of the patient when the patient interface is worn.

2. The patient interface according to claim 1, wherein when the patient interface is worn, the upper edge of the cheek contact section is closer to a median sagittal plane of the patient than the lower edge.

3. The patient interface according to claim 1, further comprising:
    a cushion assembly, configured to form an air chamber having a positive pressure near an entrance of the airway of the patient;
    an elbow assembly, adapted to deliver air generated by a fluid generator to the air chamber of the cushion assembly; and
    an adaptor member, adapted to connect the frame assembly, the cushion assembly and the elbow assembly, wherein a center of an air inlet of the elbow assembly and a center of an installation hole of the adaptor member define the mask central axis.

4. The patient interface according to claim 1, wherein each side extension arm has a first end close to the main frame and a second end away from the main frame, and a shortest distance between an upper edge and a lower edge of the first end is smaller than a shortest distance between an upper edge and a lower edge of the second end.

5. The patient interface according to claim 1, wherein each of the side extension arms further comprises:
    a frame connecting section, adapted to connect to the main frame; and
    a turning portion, located between the frame connecting section and the cheek contact section, such that the cheek contact section gets away from the mask central axis of the patient interface along a lengthwise extension direction of the cheek contact section.

6. The patient interface according to claim 1, wherein each of the side extension arms is rotatably connected on the main frame.

7. The patient interface according to claim 1, wherein each of the side extension arms further comprises a headgear connecting section for connecting the headgear.

8. The patient interface according to claim 1, wherein the headgear comprises two side straps, a top strap and a back strap; the top strap is connected between the two side straps, and each of the side straps is for detachably attaching to the headgear connecting sections of the two side extension arms; during wearing, the top strap crosses over the top of the head of the patient, and the back strap is located on a position of an occipital bone of the patient.

9. The patient interface according to claim 8, wherein in the headgear, the back strap has an elastic section, and an elongation rate of the elastic section is greater than that of other parts of the back strap.

10. The patient interface according to claim 8, wherein in the headgear, a width of the back strap is wider in the middle and narrower on two sides.

11. The patient interface according to claim 8, wherein in the headgear, a width of the top strap is wider in the middle and narrower on two sides.

12. The patient interface according to claim 1, further comprising:
    a cushion assembly, configured to form an air chamber having a positive pressure near an entrance of the airway of the patient;
    wherein, the two side extension arms are neighboring to two sides of the cushion assembly, and during wearing, the cheek contact sections of the side extension arms are between the apexes of the cheekbones and eye sockets of the patient, and fit to upper edges of upper halves of the left and right cheekbones of the patient, so as to avoid the apexes of the cheekbones and lower halves of the cheekbones of the patient.

13. The patient interface according to claim 12, wherein the side extension arms are made of a flexible material.

14. The patient interface according to claim 12, wherein each of the side extension arms has a turning portion between the nose and the cheekbone of the patient, and the turning portion has a change in curvature greater than a change in curvature of other parts of the side extension arm, and is adapted to support near a nose wing of the patient.

15. The patient interface according to claim 14, wherein a width of the turning portion is greater than a width of a frame connecting section of the side extension arm.

16. The patient interface according to claim 14, wherein a connecting line between top and bottom apexes of the turning portion is non-perpendicular to a tangent of an upper edge of the side extension arm, and non-perpendicular to a tangent of a lower edge of the side extension arm.

17. The patient interface according to claim 12, wherein the cushion assembly is configured to be inserted into nostrils, sealed in the nostrils or sealed near the nostrils of the patient.

* * * * *